US010413273B2

(12) United States Patent
Stigall et al.

(10) Patent No.: US 10,413,273 B2
(45) Date of Patent: Sep. 17, 2019

(54) INTRAVASCULAR DEVICES, SYSTEMS, AND METHODS HAVING DRIVE CABLES WITH A LUBRICIOUS COATING AND/OR RADIOPAQUE MARKERS

(71) Applicant: Koninklijke Philips N.V., Amsterdam (NL)

(72) Inventors: Jeremy Stigall, Carlsbad, CA (US); Chris LeBlanc, Carlsbad, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 831 days.

(21) Appl. No.: 14/716,462

(22) Filed: May 19, 2015

(65) Prior Publication Data
US 2015/0335309 A1    Nov. 26, 2015

Related U.S. Application Data

(60) Provisional application No. 62/000,810, filed on May 20, 2014.

(51) Int. Cl.
*A61B 8/12* (2006.01)
*A61B 8/00* (2006.01)
(Continued)

(52) U.S. Cl.
CPC .............. *A61B 8/12* (2013.01); *A61B 8/445* (2013.01); *A61B 8/4461* (2013.01);
(Continued)

(58) Field of Classification Search
CPC . A61M 25/0108; A61M 2210/12; A61B 8/12; A61B 8/445; A61B 8/4461; A61B 8/0841; A61B 8/4245; A61B 6/12
See application file for complete search history.

(56) References Cited

U.S. PATENT DOCUMENTS

| 5,095,911 A * | 3/1992 | Pomeranz ................ A61B 8/12 600/463 |
| 5,243,988 A | 9/1993 | Sieben et al. |

(Continued)

FOREIGN PATENT DOCUMENTS

| EP | 0911055 A1 | 4/1999 |
| JP | 2003061963 A | 3/2003 |

(Continued)

OTHER PUBLICATIONS

International Search Report and Written Opinion received in Patent Cooperation Treaty Application No. PCT/US2015/030791, dated Aug. 21, 2015, 12 pages.

(Continued)

*Primary Examiner* — Bo Joseph Peng

(57) ABSTRACT

Rotational intravascular ultrasound (IVUS) imaging devices and systems are provided. The IVUS imaging devices include catheters having a rotating drive cable with a transducer disposed at a distal end thereof for imaging a bodily vessel of interest. In some embodiments, a lubricious coating is applied on the drive cable to promote uniform rotation of the drive cable and the transducer. In some embodiments, the drive cable is coated with a polymer layer to promote uniform rotation of the drive cable and the transducer. In some embodiments, radiopaque markers are affixed on the drive cable for accurate placement of the transducer within of the vessel and for accurate measurement of internal dimensions and lesion lengths within the body of the patient.

13 Claims, 6 Drawing Sheets

(51) Int. Cl.
*A61M 25/01* (2006.01)
*A61B 8/08* (2006.01)
*A61B 6/12* (2006.01)

(52) U.S. Cl.
CPC ............ *A61M 25/0108* (2013.01); *A61B 6/12* (2013.01); *A61B 8/0841* (2013.01); *A61B 8/4245* (2013.01); *A61M 2210/12* (2013.01)

(56) References Cited

U.S. PATENT DOCUMENTS

| | | | |
|---|---|---|---|
| 5,259,393 | A | 11/1993 | Corso, Jr. et al. |
| 5,314,438 | A | 5/1994 | Shturman |
| 5,372,587 | A | 12/1994 | Hammerslag et al. |
| 5,380,304 | A * | 1/1995 | Parker ............... A61M 25/0012 138/138 |
| 5,546,948 | A | 8/1996 | Hamm et al. |
| 5,606,981 | A | 3/1997 | Tartacower et al. |
| 5,666,969 | A | 9/1997 | Urick et al. |
| 5,711,909 | A | 1/1998 | Gore et al. |
| 5,728,042 | A | 3/1998 | Scwager |
| 5,738,100 | A * | 4/1998 | Yagami .................... A61B 8/12 600/459 |
| 5,835,563 | A | 11/1998 | Navab et al. |
| 6,221,066 | B1 * | 4/2001 | Ferrera ............ A61B 17/12022 606/1 |
| 6,261,630 | B1 | 7/2001 | Nazarova et al. |
| 6,575,991 | B1 | 6/2003 | Chesborough et al. |
| 6,641,540 | B2 | 11/2003 | Fleischman et al. |
| 7,169,140 | B1 | 1/2007 | Kume |
| 8,104,479 | B2 | 1/2012 | Glynn et al. |
| 8,403,856 | B2 | 3/2013 | Corl |
| 8,864,674 | B2 | 10/2014 | Corl |
| 9,743,992 | B2 | 8/2017 | Stigall et al. |
| 2004/0019318 | A1 | 1/2004 | Wilson et al. |
| 2007/0016063 | A1 * | 1/2007 | Park ................... A61M 25/0158 600/459 |
| 2008/0091140 | A1 | 4/2008 | Hamburger |
| 2009/0030312 | A1 | 1/2009 | Hadjicostis |
| 2009/0264759 | A1 | 10/2009 | Byrd |
| 2009/0292199 | A1 | 11/2009 | Bielewicz et al. |
| 2010/0331697 | A1 | 12/2010 | Webler et al. |
| 2011/0224650 | A1 * | 9/2011 | Itou .......................... A61B 8/12 604/524 |
| 2012/0116503 | A1 | 5/2012 | Grewe et al. |
| 2014/0058257 | A1 | 2/2014 | Stigall et al. |
| 2014/0234736 | A1 | 4/2014 | Otsuka et al. |
| 2014/0276027 | A1 | 9/2014 | Gaddis et al. |
| 2014/0276687 | A1 | 9/2014 | Goodman et al. |

FOREIGN PATENT DOCUMENTS

| | | |
|---|---|---|
| JP | 2003062082 A | 3/2003 |
| JP | 2007061311 A | 3/2007 |
| JP | 2014064837 A | 4/2014 |
| WO | 9524237 A2 | 9/1995 |
| WO | 0038580 A1 | 7/2000 |
| WO | 2006058223 A2 | 1/2006 |
| WO | 2012009518 A1 | 1/2012 |

OTHER PUBLICATIONS

International Search Report and Written Opinion received in Patent Cooperation Treaty Application No. PCT/US2013/056193, dated Nov. 7, 2013, 10 pages.

* cited by examiner

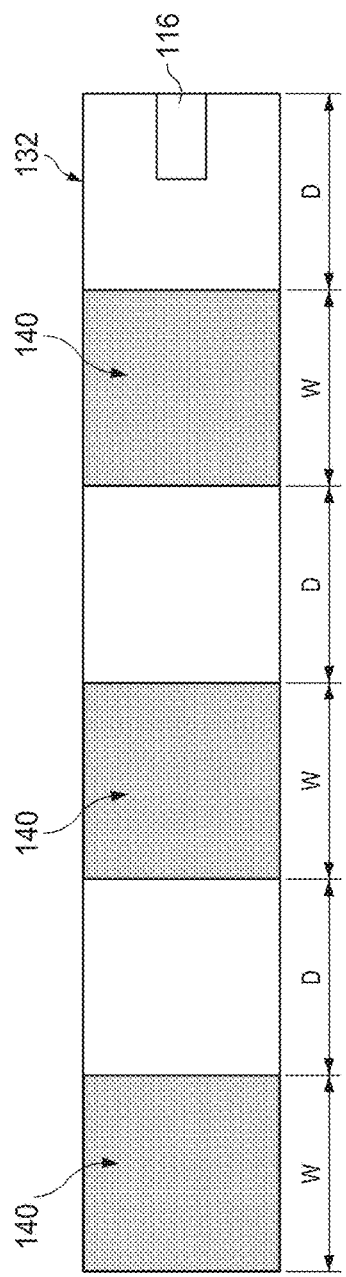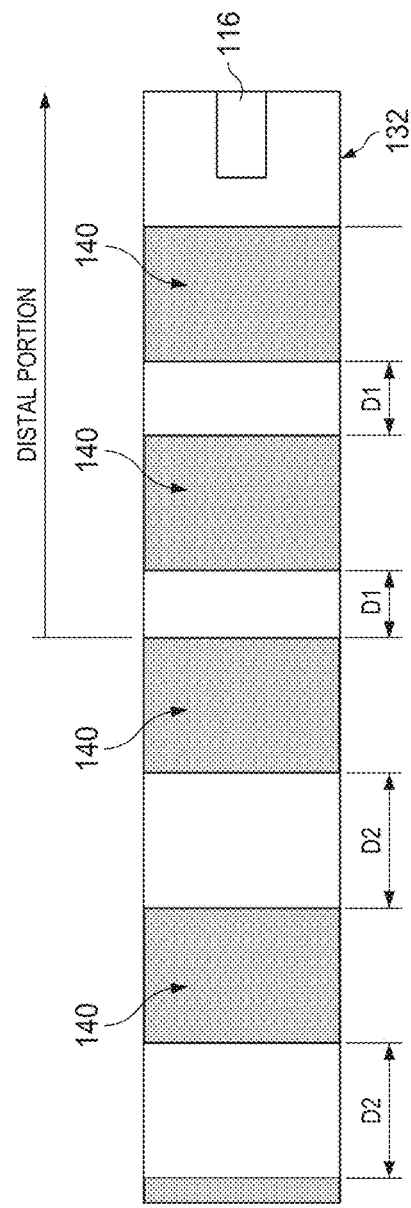
Fig. 4A
Fig. 4B

INTRAVASCULAR DEVICES, SYSTEMS, AND METHODS HAVING DRIVE CABLES WITH A LUBRICIOUS COATING AND/OR RADIOPAQUE MARKERS

CROSS REFERENCE TO RELATED APPLICATIONS

The present application claims priority to and the benefit of the U.S. Provisional Patent Application No. 62/000,810, filed May 20, 2014, which is hereby incorporated by reference in its entirety.

FIELD OF DISCLOSURE

The present disclosure generally relates to intravascular devices, such as catheters and guide wires, used in clinical diagnostic and therapeutic procedures, including intravascular ultrasound (IVUS) procedures. These intravascular devices can include a flexible drive cable having a transducer disposed at a distal end thereof for imaging a vessel of interest. During the IVUS procedure, the drive cable and the transducer may be rotated within the intravascular device to allow capturing of multiple images of the vessel. Embodiments of the present disclosure include a lubricious coating on the drive cable to promote uniform rotation of the drive cable and the transducer by reducing rotational friction experienced by the drive cable. Embodiments of the present disclosure include radiopaque markers on the drive cable, or defined by the drive cable, for accurate estimation of lesion lengths within the body of the patient and for accurate placement of the transducer within of the vessel.

BACKGROUND

IVUS imaging procedures are widely used in interventional cardiology as a diagnostic tool for assessing a vessel, such as an artery, within the body of the patient to determine the need for treatment, to guide intervention, and/or to assess the effectiveness of administered treatment. An IVUS imaging system uses ultrasound echoes to form a cross-sectional image of the vessel of interest. Typically, IVUS imaging uses a transducer in a catheter to emit ultrasound signals (waves) and to receive the reflected ultrasound signals. The emitted ultrasound signals (often referred to as ultrasound pulses) pass easily through most tissues and blood, but they are partially reflected by discontinuities arising from tissue structures (such as the various layers of the vessel wall), red blood cells, and other features of interest. The IVUS imaging system, which is connected to the catheter by way of a patient interface module, processes the received ultrasound signals (often referred to as ultrasound echoes) to produce a cross-sectional image of the vessel proximate to where the catheter is located.

The two types of catheters in common use today are solid-state and rotational. A conventional solid-state catheter may use an array of transducers (typically 64) distributed around a circumference of a sheath, which is an outer layer of the catheter. The transducers are connected to an electronic multiplexer circuit. The multiplexer circuit selects transducers from the array for transmitting ultrasound signals and receiving reflected ultrasound signals. By stepping through a sequence of transmit-receive transducer pairs, the solid-state catheter can synthesize the effect of a mechanically scanned transducer element, but without moving parts. Since there is no rotating mechanical element, the transducer array can be placed in direct contact with blood and vessel tissue with minimal risk of vessel trauma, and the solid-state scanner can be wired directly to the IVUS imaging system with a simple electrical cable and a standard detachable electrical connector.

On the other hand, a conventional rotational catheter may include a flexible drive cable that continually rotates inside the sheath of the catheter inserted into the vessel of interest. The drive cable may have a transducer disposed at a distal end thereof. The transducer is typically oriented such that the ultrasound signals propagate generally perpendicular to an axis of the catheter. In the typical rotational catheter, the sheath may be filled with fluid (e.g., saline) to protect the vessel tissue from the rotating drive cable and transducer while permitting ultrasound signals to freely propagate from the transducer into the tissue and back. As the drive cable rotates (e.g., at 30 revolutions per second), the transducer is periodically excited with a high voltage pulse to emit a short burst of ultrasound. The ultrasound signals are emitted from the transducer, through the fluid-filled sheath and sheath wall, in a direction generally perpendicular to an axis of rotation of the drive cable (i.e., the axis of the IVUS catheter). The transducer then listens for returning ultrasound signals reflected from various tissue structures, and the IVUS imaging system assembles a two dimensional image of the vessel cross-section from a sequence of several hundred of these ultrasound pulse/echo acquisition sequences occurring during a single revolution of the drive cable and the transducer.

However, the images obtained by the conventional rotational catheters exhibit distortion caused due to non-uniform rotational distortion (NURD). The distorted images fail to provide the required insight into the vessel condition. NURD may occur due to, for example, friction between the drive cable and the sheath that encloses the drive cable; friction between the sheath and the vessels through which the catheter travels through during use; non-symmetrical drive cable/transducer assembly that causes the drive cable to resist bending more at some angles than at other angles (when rotated, these asymmetries cause the drive cable to store more energy in some angular orientations and then to release that energy as the drive cable is rotated past that angle); the sheath and drive cable containing various bends and twists along its path to the vessel of interest, resulting in the transducer rotating at a non-uniform angular velocity even though the drive cable is rotated at a constant speed. As such, the conventional rotational catheters fail to adequately minimize non-uniform rotational distortion, while also providing sufficient strength and flexibility.

Intravascular devices are also used diagnostically to measure internal body dimensions, estimate lesion lengths, and to ensure accurate placement of the intravascular device within the body of the patient. In several of these procedures, it is advantageous to be able to visualize the progress of the transducer, which enables the imaging, towards the target location within the body of the patient. Introducing intravascular devices into the body often requires fluoroscopic visualization to aid the treating healthcare provider in guiding the intravascular device to the target site. Intravascular devices are commonly formed of a non-radiopaque polymeric material. Therefore, radiopaque markers are affixed at a distal end of the intravascular device to enable the intravascular device to be visualized during x-ray and fluoroscopic procedures. For example, in intravascular procedures, health care providers may guide the intravascular device to a target location by using fluoroscopy to track the position of radiopaque markers on distal end of the intravascular device.

Conventionally, these radiopaque markers are circumferential metallic bands affixed to the exterior surface of the intravascular device. Although these marker bands allow the distal end of the intravascular devices to be visualized by fluoroscopy, they present certain problems. First, affixing of the radiopaque markers to the exterior surface of the sheath of the catheter fails to provide guidance as to the accurate position of the included transducer that enables the imaging within the body of the patient. The operator is undesirably left to guess or estimate the position of the transducer during the imaging procedure. Further, metallic marker bands require affixing (e.g., by crimping, swaging, or adhesive) to the underlying intravascular device to avoid slippage as the intravascular device is moved through the body. The bands may protrude from the tubular surface of the intravascular device and increase the intravascular device profile, which creates frictional resistance to the translational movement of the intravascular device through body passages, and potentially damages tissues contacting the moving intravascular device. In some instances, where a marker band has been swaged onto the exterior surface of the intravascular device, and the inner diameter of a marker band is greater than the outer diameter of the intravascular device, buckling may occur, causing the marker band to crack and the exterior surface to tear. Finally, the placement of band markers on the outer surface presents problems with inadvertent disassociation of the markers from the intravascular device, with attendant loss of positional and measurement accuracy. In addition, such marker bands are constructed from expensive and heavy radiopaque metals such as gold, platinum, tantalum, and alloys of these dense materials. The use of these heavy materials typically results in inflexible and rigid marker bands that can impair the trackability of the catheter by increasing the stiffness of the intravascular device, thereby compromising the flexibility and maneuverability of the intravascular device. As such, the conventional intravascular device with radiopaque markers affixed to the exterior surface fail to enable accurate measurement of internal body dimensions, accurate estimation of lesion lengths, and accurate placement of the transducer within the body of the patient.

Accordingly, there remains a need for improved ultrasound intravascular devices for use in IVUS imaging and associated devices, systems, and methods. The devices, systems, and methods proposed in the present disclosure overcome one or more of the deficiencies of conventional intravascular devices.

SUMMARY

In one aspect, the present disclosure provides a device including a drive cable to rotate about an axis of rotation associated with the IVUS device and a transducer coupled to a distal end of the flexible drive cable such that the transducer rotates with the drive cable. The drive cable may be a hollow flexible coil and may be coated with a lubricious coating. The lubricious coating may be a hydrophobic or a hydrophilic coating or solution. The drive cable may be coated with the lubricious material by dipping the drive cable in the lubricious coating, by rolling the drive cable in the lubricious coating, or by applying the lubricious coating on the drive cable with a wipe. In one embodiment, the drive cable may be surrounded by a polymer layer. The polymer layer can be formed of any suitable material, including high density polyimide and low density polyimide. The transducer may be coupled to the flexible drive cable by two or more layers of counter wound stainless steel wires. The device may include an interface module to provide, over a rotational interface, a first control signal to enable rotation of the drive cable, and a second control signal to regulate operation of the transducer. The device may also include an integrated circuit (IC) electrically coupled to the transducer, the IC being located at the distal end of the drive cable. In one embodiment, the IC may include an amplifier, a transmitter, and protection circuitry. The device may include a catheter assembly to at least partially enclose the drive cable. The catheter assembly may include a polymer layer that surrounds the drive cable. The drive cable may include a plurality of radiopaque markers. In some embodiments, the drive cable includes the plurality of radiopaque markers adjacent to the distal end of the drive cable, and in another embodiment, the drive cable includes the plurality of radiopaque markers along a majority or the entire length of the drive cable. The plurality of radiopaque markers may be of equal or variable size. Similarly, the plurality of radiopaque markers may be spaced equidistantly or variably along the drive cable. In one embodiment, a width of a radiopaque marker may be substantially equal to or proportional to a distance between two adjacent radiopaque markers.

In one aspect, the present disclosure provides a device including a drive cable to rotate about an axis of rotation associated with the IVUS device and a transducer coupled to a distal end of the flexible drive cable such that the transducer rotates with the drive cable, wherein a polymer layer encloses the drive cable without enclosing the transducer. In one embodiment, the polymer layer may be fixedly secured to and surrounding the drive cable without enclosing the transducer. The device may contain a catheter assembly that includes the polymer layer, which may be formed of any suitable material including a polyimide ethylene, a high density polyimide, or a low density polyimide. In some embodiments, the polymer may be coated with a lubricious coating. The lubricious coating may be a hydrophobic or a hydrophilic coating or solution. Further, the drive cable may include a plurality of radiopaque markers. In some embodiments, the drive cable includes the plurality of radiopaque markers adjacent to the distal end of the drive cable, and in another embodiment, the drive cable includes the plurality of radiopaque markers along a majority or the entire length of the drive cable. The plurality of radiopaque markers may be of equal or variable size. Similarly, the plurality of radiopaque markers may be spaced equidistantly or variably along the drive cable. In one embodiment, a width of a radiopaque marker may be substantially equal to or proportional to a distance between two adjacent radiopaque markers.

In another aspect, the present disclosure provides a device including a drive cable configured to rotate about an axis of rotation associated with the IVUS device and a transducer coupled to a distal end of the flexible drive cable such that the transducer rotates with the drive cable, wherein the drive cable includes a plurality of radiopaque markers. The plurality of the radiopaque markers may be flexible to conform to the flexibility of the drive cable. In some embodiments, the drive cable includes the plurality of radiopaque markers adjacent to the distal end of the drive cable, and in another embodiment, the drive cable includes the plurality of radiopaque markers along a majority or the entire length of the drive cable. The plurality of radiopaque markers may be of equal or variable size. Similarly, the plurality of radiopaque markers may be spaced equidistantly or variably along the drive cable. In some embodiments, a width of a radiopaque marker may be substantially equal to or proportional to a distance between two adjacent radiopaque markers. Further, a first distance between two adjacent radiopaque markers located at the distal end of the drive cable may be smaller than a second distance between two adjacent radiopaque markers located at the proximal end of the drive cable. The plurality of radiopaque markers provide varying radiopacity of known dimensions at known distances on the drive cable to allow accurate placement of the transducer and accurate measurement of desired anatomical structures.

In some embodiments, the drive cable may include the plurality of radiopaque markers in the form of an alternating series of tightly wound sections and loosely wound sections of the drive cable. The tightly wound sections may comprise areas of a closed pitch and the loosely wound sections may comprise areas of an open pitch. Also, the tightly wound sections may be uniformly or variably spaced from each other by the loosely wound sections. In one embodiment, the tightly wound sections and/or the loosely wound sections may be of respective uniform lengths.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure. Throughout this description, like elements, in whatever embodiment described, refer to common elements wherever referred to and referenced by the same reference number. The characteristics, attributes, functions, interrelations ascribed to a particular element in one location apply to those elements when referred to by the same reference number in another location unless specifically stated otherwise.

The figures referenced below are drawn for ease of explanation of the basic teachings of the present disclosure only; the extensions of the figures with respect to number, position, relationship, and dimensions of the parts to form the following embodiments will be explained or will be within the skill of the art after the following description has been read and understood. Further, the exact dimensions and dimensional proportions to conform to specific force, weight, strength, and similar requirements will likewise be within the skill of the art after the following description has been read and understood.

The following is a brief description of each figure used to describe the present disclosure, and thus, is being presented for illustrative purposes only and should not be limitative of the scope of the present disclosure.

Figure 1:
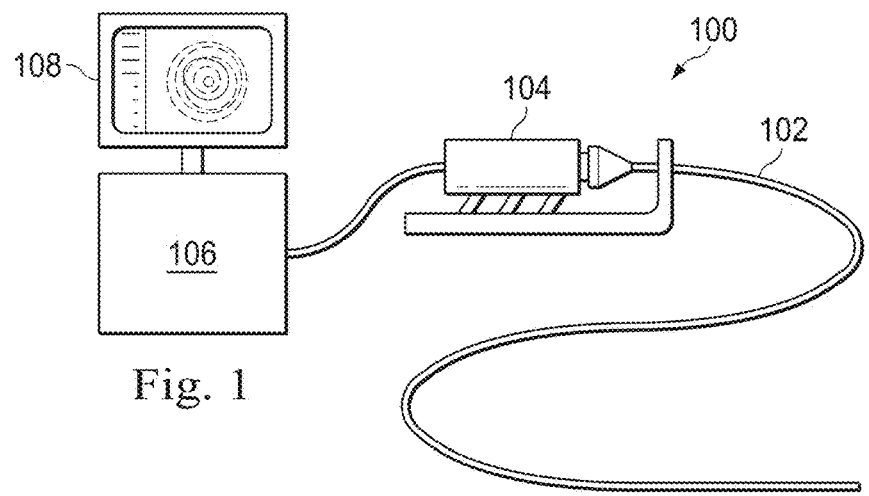

FIG. 1 illustrates an exemplary imaging system according to an embodiment of the present disclosure.

Figure 2:
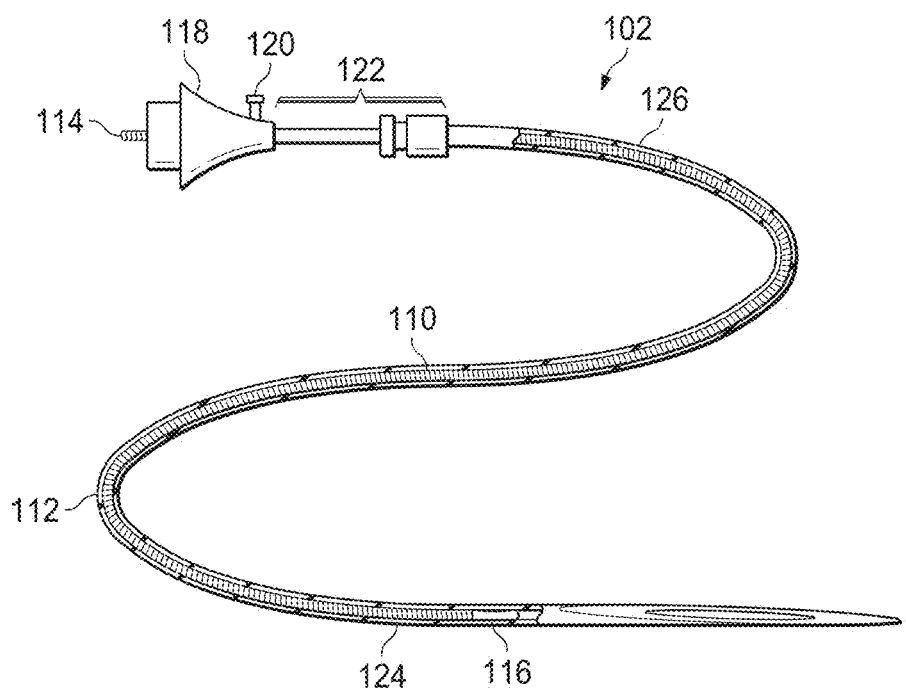

FIG. 2 illustrates a partial cutaway perspective view of an exemplary imaging device according to an embodiment of the present disclosure.

Figure 3A:
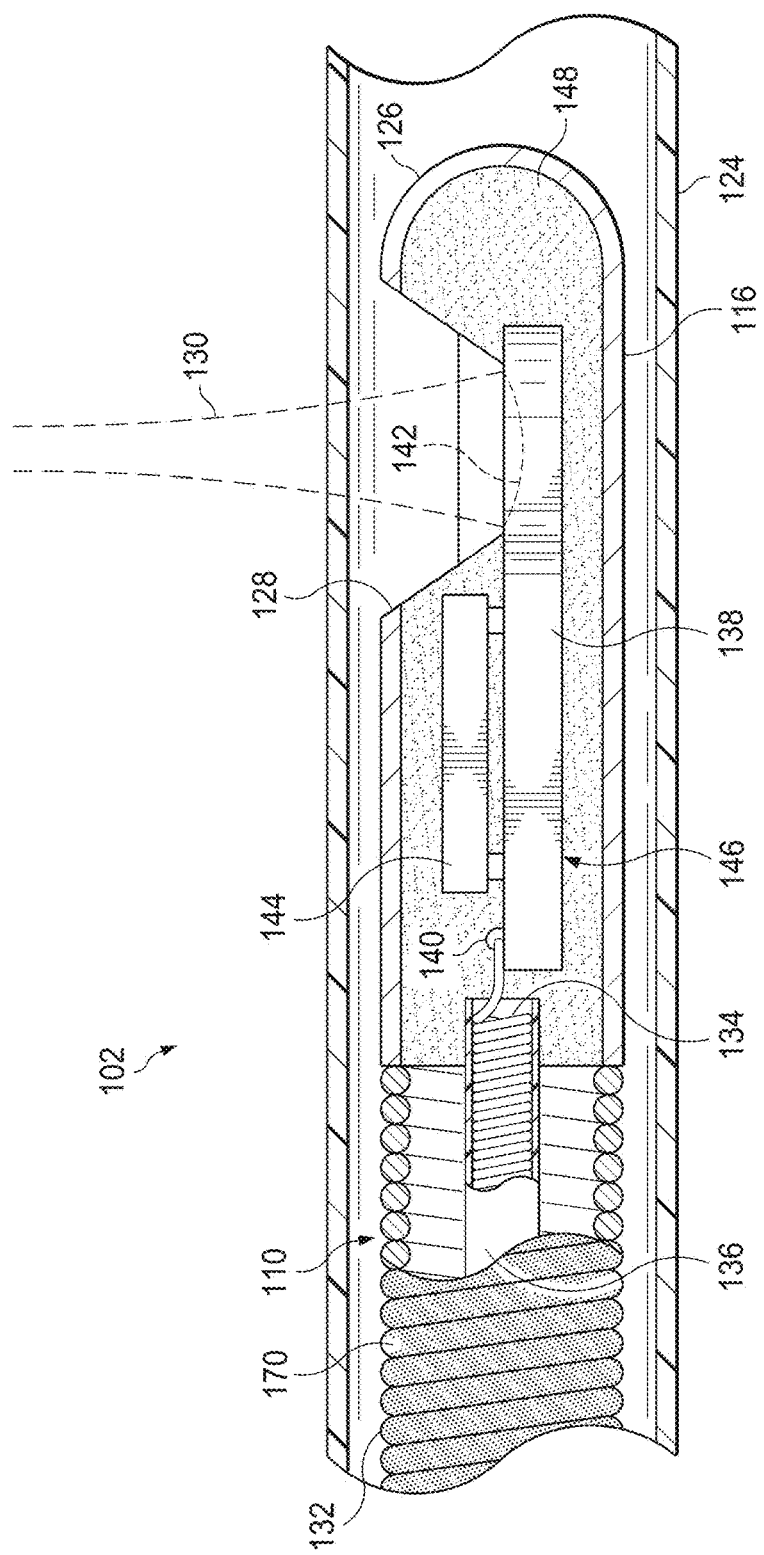
Figure 3B:
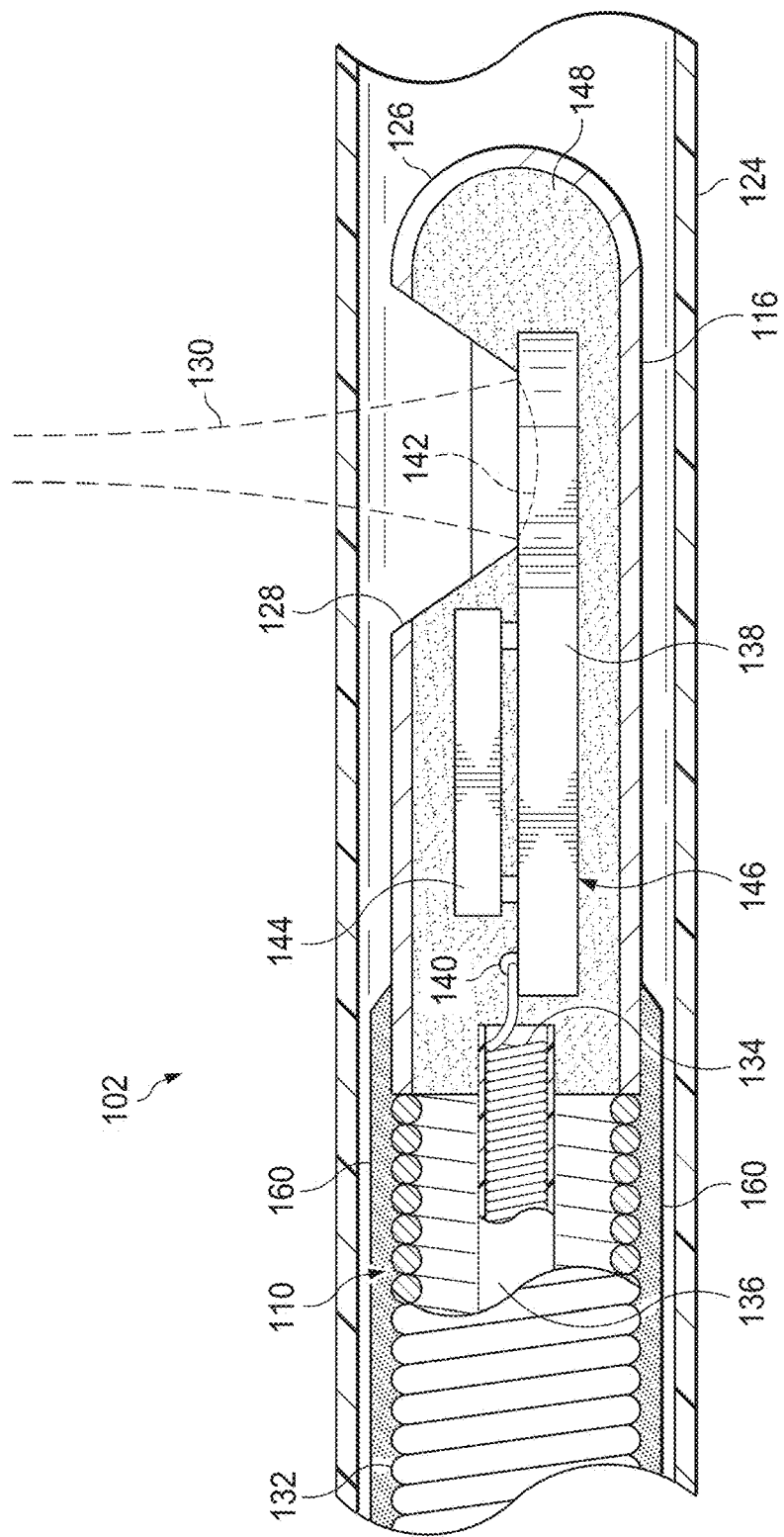

FIGS. 3A and 3B illustrate cross-sectional side views of portions of exemplary catheters according to embodiments of the present disclosure.

FIGS. 4A and 4B illustrate exemplary drive cables according to embodiments of the present disclosure.

Figure 5:
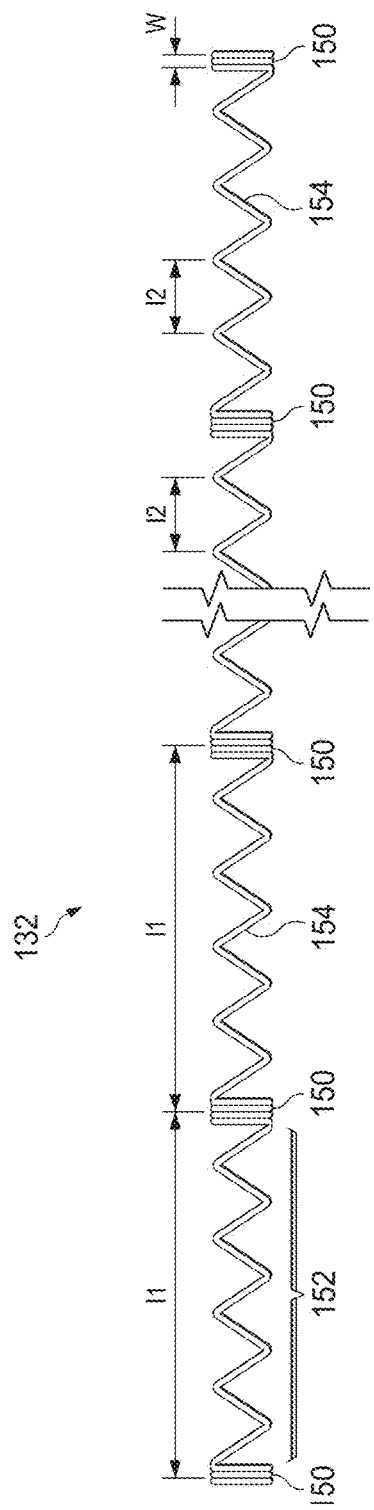

FIG. 5 illustrates another exemplary drive cable according to an embodiment of the disclosure.

Figure 6A:
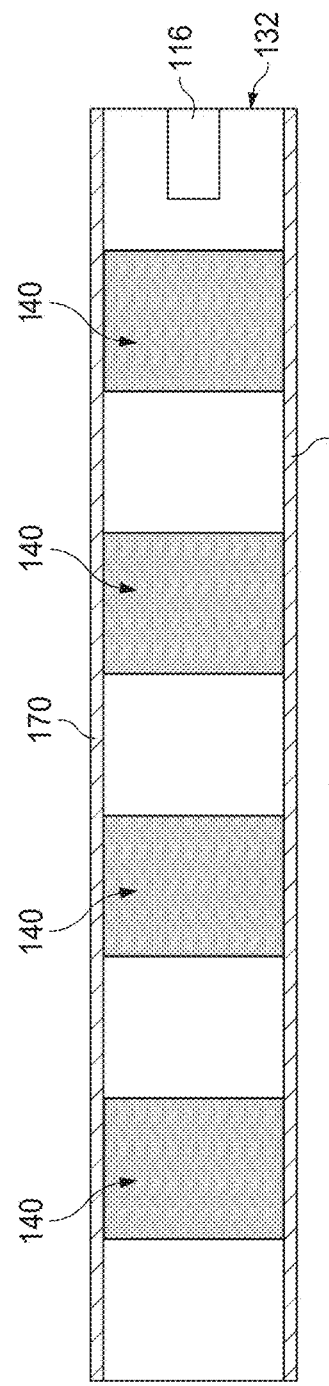
Figure 6B:
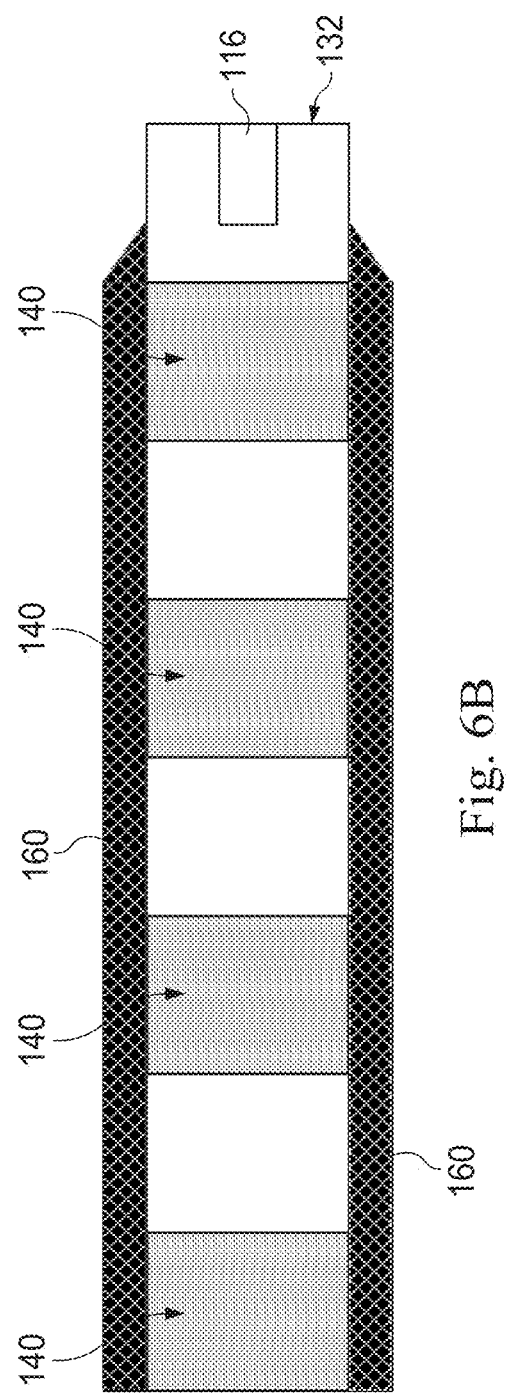

FIGS. 6A and 6B illustrate cross-sectional side views the exemplary drive cable according to embodiments of the present disclosure.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately. For simplicity, in some instances the same reference numbers are used throughout the drawings to refer to the same or like parts.

As discussed above, there remains a need for improved ultrasound intravascular devices to be used in IVUS imaging procedures and associated devices, systems, and methods. The present disclosure describes devices, systems, and methods to reduce non-uniform rotational distortion and also to accurately measure internal body dimensions, accurately estimate lesion lengths, and accurately place the transducer within the body of the patient. In particular, the present disclosure provides a lubricious coating applied to the drive cable to promote uniform rotation of the drive cable and the transducer by minimizing non-uniform rotation distortion and by reducing rotational friction between the rotating drive cable and (i) the fluid filled in the sheath of the catheter, and/or (ii) the inner surface of the sheath of the catheter. Further, the present disclosure provides radiopaque markers on the drive cable (or defined by the drive cable) to accurately measure internal body dimensions, accurately estimate lesion lengths, and/or accurately place the transducer within the body of the patient.

Referring to FIG. 1, shown therein is an IVUS imaging system 100 according to an embodiment of the present disclosure. The IVUS system can utilize any type of suitable IVUS imaging device 102, including rotational and/or phased array based devices. In some particular embodiments, the present disclosure incorporates a focusing transducer. The transducer may be a piezoelectric micromachined ultrasound transducer (PMUT) fabricated on a microelectromechanical system (MEMS) substrate using a polymer piezoelectric material, for example as disclosed in U.S. patent application Ser. No. 13/892,045, filed May 10, 2013, and/or U.S. Pat. No. 6,641,540, each of which is hereby incorporated by reference in its entirety. In some embodiments of the present disclosure, the IVUS imaging system 100 is a PMUT rotational IVUS imaging system. In that regard, the main components of the PMUT rotational IVUS imaging system include the PMUT rotational IVUS catheter 102, a PMUT catheter compatible patient interface module (PIM) 104, an IVUS console or processing system 106, and a monitor 108 to display the IVUS images generated by the IVUS console 106. Generally, the catheter 102 may be configured to take on any desired arcuate profile when in the curved configuration. In one instance, the catheter 102 may have an overall length of at least 90 cm, and in some embodiments, extending to 150 cm. Larger lengths of the catheter 102 are also contemplated. Also, the catheter 102 may have an external diameter ranging from 2 F to 9 F (i.e., 0.67 mm to 3 mm). As discussed in greater detail below, the PMUT rotational IVUS catheter 102 includes a PMUT ultrasound transducer along with its associated circuitry mounted near a distal tip of the catheter and the appropriate electrical connector to support the rotational interface. The PMUT-compatible PIM 104 generates and/or provides the required sequence of transmit trigger signals and control waveforms to regulate the operation of the circuit and processes the amplified echo signals received over that same conductor pair. The PMUT-compatible PIM 104 also supplies the high- and low-voltage DC power supplies to support operation of the PMUT rotational IVUS catheter 102. The PMUT-compatible PIM 104 allows delivery of DC supply voltages to the PMUT circuitry of the catheter 102 across a rotational interface. This feature largely precludes the requirement of a rotary transformer, commonly used for traditional rotational IVUS systems, since a transformer can only convey AC signals from the primary to the secondary side. Practical options for delivering DC power across a rotating interface include the use of slip-rings and/or the implementation of the active spinner technology described in U.S. Patent Application Publication No. 2010/0234736, which is hereby incorporated by reference in its entirety.

Referring now to FIG. 2, shown therein is a diagrammatic, partial cutaway perspective view of the PMUT catheter 102 according to an embodiment of the present disclosure. In that regard, FIG. 2 shows additional detail regarding the construction of the PMUT rotational IVUS catheter 102. In many respects, this catheter is similar to traditional rotational IVUS catheters, such as the Revolution® catheter available from Volcano Corporation and described in U.S. Pat. No. 8,104,479, or those disclosed in U.S. Pat. Nos. 5,243,988 and 5,546,948, each of which is hereby incorporated by reference in its entirety. In that regard, the PMUT rotational IVUS catheter 102 includes an imaging core 110 and an outer catheter/sheath assembly 112. The imaging core 110 includes a flexible drive cable 132 that is terminated at the proximal end by a rotational interface 114 providing electrical and mechanical coupling to the PIM 104 of FIG. 1. As such, the drive cable 132 is at least partially enclosed in the catheter/sheath assembly 112. The distal end of the flexible drive cable 132 of the imaging core 110 is coupled to a transducer housing 116 containing the PMUT and associated circuitry, which are described in greater detail below. The catheter/sheath assembly 112 includes a hub 118 that supports the rotational interface and provides a bearing surface and a fluid seal between the rotating and non-rotating elements of the catheter assembly. The hub 118 includes a luer lock flush port 120 through which saline is injected to flush out the air and fill the inner lumen of the sheath with an ultrasound-compatible fluid at the time of use of the catheter. The saline or other similar flush is typically required since air does not readily conduct ultrasound. Saline also provides a biocompatible lubricant for the rotating drive cable. The hub 118 is coupled to a telescope 122 that includes nested tubular elements and a sliding fluid seal that permit the catheter/sheath assembly 112 to be lengthened or shortened to facilitate axial movement of the transducer housing within an acoustically transparent window 124 of the distal portion of the catheter 102. In some embodiments, the window 124 includes thin-walled plastic tubing fabricated from material(s) that readily conduct ultrasound waves between the transducer and the vessel tissue with minimal attenuation, reflection, or refraction. A proximal shaft 126 of the catheter/sheath assembly 112 bridges the segment between the telescope 122 and the window 124, and includes a material or composite that provides a lubricious internal lumen and optimum stiffness, but without the need to conduct ultrasound.

Referring now to FIG. 3A, shown therein is a cross-sectional side view of a distal portion of the catheter 102 according to an embodiment of the present disclosure. In particular, FIG. 3A shows an expanded view of aspects of the distal portion of the imaging core 110. In this exemplary embodiment, the imaging core 110 is terminated at its distal tip by a housing 116 fabricated from stainless steel and provided with a rounded nose 126 and a cutout 128 for the ultrasound beam 130 to emerge from the housing 116. In some embodiments, the flexible drive cable 132 of the imaging core 110 includes two or more layers of counter wound stainless steel wires, welded, or otherwise secured to the housing 116 such that rotation of the flexible drive cable also imparts corresponding rotation on the housing 116. In the illustrated embodiment, the PMUT MEMS 138 includes a spherically focused transducer 142 and carries an application-specific integrated circuit (ASIC) 144. The ASIC 144 is electrically coupled to the PMUT MEMS 138 through two or more connections. In that regard, in some embodiments of the present disclosure the ASIC 144 includes an amplifier, a transmitter, and a protection circuit associated with the PMUT MEMS. In some embodiments, the ASIC 144 is flip-chip mounted to the substrate of the PMUT MEMS 138 using anisotropic conductive adhesive or suitable alternative chip-to-chip bonding method. When assembled together the PMUT MEMS 138 and the ASIC 144 form an ASIC/MEMS hybrid assembly 146 that is mounted within the housing 116. An electrical cable 134 with optional shield 136 is attached to the ASIC/MEMS hybrid assembly 146 with solder 140. The electrical cable 134 extends through an inner lumen of the flexible drive cable 132 to the proximal end of the imaging core 110 where it is terminated to the electrical connector portion of the rotational interface 114 shown in FIG. 2. In an embodiment, the length of the typical electrical cable 134 may range from 120.0 cm to 200.0 cm. The ASIC/MEMS hybrid assembly 146 may be secured in place relative to the housing 116 by an epoxy 148 or other bonding agent. The epoxy 148 may also serve as an acoustic backing material to absorb acoustic reverberations propagating within the housing 116 and as a strain relief for the electrical cable 134 where it is soldered to the ASIC/MEMS hybrid assembly 146.

In an exemplary embodiment, the drive cable 132 may be a hollow flexible coil. The drive cable 132 may be coated with a lubricious coating 170. The drive cable 132 may be coated by, for example, dipping the drive cable 132 in the lubricious coating 170, by rolling the drive cable 132 in the lubricious coating 170, or by applying the lubricious coating 170 on the drive cable 132 with, for example, a wipe. In one embodiment, the lubricious coating 170 may be adhered to the drive cable 132 by using ultra-violet (UV) intensity, and may be used in conjunction with or along with a primer. The lubricious coating 170 may be a hydrophilic or hydrophobic solution. Further, the lubricious coating 170 may be a water-based or a solvent-based coating.

The lubricious coating may have very low frictional properties to promote uniform rotation of the drive cable 132 and the transducer 142 by reducing any static or dynamic frictional forces experienced by the rotating drive cable 132.

For example, the lubricious coating 170 may substantially reduce the surface energy interactions between the rotating drive cable 132 and the inner walls of the sheath 112 and/or any fluid positioned therebetween. Applying the lubricious coating directly to the rotating drive cable 132 reduces and/or eliminates NURD and allows the drive cable 132 and the transducer 142 to predictably rotate at a more uniform angular velocity even when the rotating drive cable 132 comes in contact with the surrounding surfaces. Also, the reduction in friction assists in expediting the imaging procedure and in minimizing patient trauma.

Referring now to FIG. 3B, shown therein is a cross-sectional side view of a distal portion of the catheter 102 according to an embodiment of the present disclosure. The catheter 102 illustrated in FIG. 3B is identical with respect to the catheter 102 illustrated in FIG. 3A except that the catheter 102 illustrated in FIG. 3B includes a polymer layer 160. The polymer layer 160 may be fixedly secured to the drive shaft 132 so that it is positioned between the sheath 112 and the imaging core 110 to facilitate low-friction, uniform rotation of the drive cable transducer 142. The polymer layer 160 can be formed of a material having less friction than the drive cable 132. For example, the polymer layer 160 may include high-density polyimide ethylene (HDPE) material, low-density polyimide ethylene (LDPE) material, or polyimide ethylene (PE) material. The polymer layer 160 may also include nylon, pebax, or any other common metric material. In some embodiments, the polymer layer 160 is coated with the lubricious coating 170 to further reduce any frictional forces with respect to the polymer layer 160 and the surrounding sheath and/or fluids.

FIG. 4A illustrates an exemplary drive cable 132 according to an embodiment of the disclosure. The drive cable 132 may include a plurality of radiopaque markers 140. In one embodiment, a predetermined number of individual coils of the drive cable 132, which are separated by a predetermined distance, may be coated with radiopaque material to induce radiopaque markers 140 on the drive cable 132. In another embodiment, the radiopaque markers may be circumferential bands, having predetermined widths, affixed on the outer surface of the drive cable 132 at predetermined distances. These circumferential bands may also be flexible to conform to the flexibility of the drive cable 132. The radiopaque markers may be separate elements fixedly secured to the drive cable.

In one embodiment, the drive cable 132 may include the plurality of radiopaque markers 140 at a distal end of the drive cable 132. In another embodiment, the drive cable 132 may include the plurality of radiopaque markers 140 along a majority or the entire length of the drive cable 132. The radiopaque markers may be of equal or variable size and may be placed equidistantly or variably along the drive cable 132. In that regard, each radiopaque marker may have a predetermined width (W) ranging from 0.5 mm to 1.0 cm and may be placed at a predetermined distance(s) (D) ranging from 1.0 mm to 150.0 cm. In some embodiments, the width W of the radiopaque markers may be substantially the same as the spacing distance D, but in other embodiments, the width W may vary in accordance with the desired application for the radiopaque markers. In one embodiment, the width W may be proportional to the distance D. Also, as illustrated in FIG. 4B, the radiopaque markers may be placed at varying distances based on their location on the drive cable 132. For example, a first distance (D1) between the radiopaque markers at the distal end of the drive cable 132 may be smaller than a second distance (D2) between the radiopaque markers at a more proximal location along the length of the drive cable 132. The distance D1 may range from 1.0 mm to 10.0 cm and the distance D2 may range from 1.0 cm to 50.0 cm. In another embodiment, the distances between the radiopaque markers may progressively decrease from the proximal end to the distal end of the drive cable 132.

As discussed above, the present disclosure proposes affixing radiopaque markers to the drive cable 132 (instead of the exterior surface of the sheath of the catheter) for accurately placing the transducer within the body of the patient. It is advantageous to affix the radiopaque markers to the drive cable 132 because this enables the operator to accurately observe and track the position of the transducer 142, relative to the known positions of the radiopaque markers 140 on the drive cable, once the catheter 102 is inserted in the body of the patient. The knowledge of the accurate position of the transducer 142 allows accurate placement of the transducer 142 at the desired locations within the vessel of interest for imaging. This reduces instances where an operator must guess or estimate the location of the transducer 142 in the catheter 102 during the imaging procedure. As such, the overall efficiency of the imaging procedure is increased. Further, affixing the radiopaque markers to the drive cable 132 enables accurately measuring internal body dimensions, and accurately estimating lesion lengths. In particular, the strategically designed placement of the radiopaque markers of known dimensions at known distances along the length of the drive cable 132 allows the operator to use the radiopaque markers to accurately measure internal body dimensions and lesion lengths. The accurate measurement of these anatomical structures may assist the health care provider in diagnosing a condition, deciding on the appropriate course of treatment, treating the condition, and evaluating the results of the treatment. The radiopaque markers can also be utilized to track the position of the intravascular device and/or the transducer to facilitate co-registration of the images obtained with the intravascular device to other types of intravascular or extravascularly obtained patient data.

Additional advantages may be realized by affixing the radiopaque markers to the drive cable 132. In particular, the drive cable 132 does not come in direct contact with the body passages since the drive cable 132 is surrounded by fluid and the sheath 112 of the catheter 102. As such, any instance of trauma to the body tissue is minimized even if the radiopaque markers protrude or buckle because the protrusions would be contained by the sheath 112. Also, the risk of disassociation of the radiopaque markers from the drive cable 132 due to friction with the bodily passages is minimal for the same reason that the drive cable 132 is surrounded by low friction fluid. Therefore, affixing the radiopaque markers directly to the drive cable 132 again increases the overall efficiency and safety of the imaging procedure.

FIG. 5 illustrates another exemplary drive cable 132 according to an embodiment of the disclosure. In this embodiment, the drive cable 132 may define radiopaque markers in the form of tightly wound sections 150 separated by the loosely wound sections 152. The drive cable 132 may be formed of a single length of material that has been wound into areas of varying pitch and coated with a radiopaque material. Alternatively, the entire portion of the drive cable 132 defining the radiopaque markers can be formed of a radiopaque material. The radiopaque material may be one or more radiopaque metals including, but not limited to, gold, tungsten, iridium, rhodium, platinum, barium, bismuth, and combinations and/or alloys thereof. In some embodiments, the radiopaque material is a radiopaque polymer, which may comprise a matrix of a polymeric material in combination with a radiopaque metal. Any material with a high enough radiodensity when shaped into a tightly wound section 150 can be used. For example, the drive cable 132 may be formed of lower cost alternatives to precious metals with equivalent radiodensity.

The tightly wound sections 150 are tightly wound areas of the drive cable 132 that form blocks of greater radiopacity or radiodensity with respect to the loosely wound sections 152. As such, the tightly wound sections of the radiopaque element are ultrasonically recognizable to the imaging device. In some embodiments, the tightly wound sections 150 have a width (W) ranging from 1.0 mm to 2.0 mm. Both the tightly wound sections 150 and the loosely wound sections 152 retain the ability to flex. The tightly wound sections 150 may have greater widths W (and greater resultant visibility) than rigid, metallic marker bands. Thus, the tightly wound sections 150 form flexible radiopaque markers that are capable of curving with the catheter 102 as it traverses through tortuous anatomy without causing the inadvertent catheter kinking and/or trauma that can be caused by rigid marker bands.

The tightly wound sections 150 have a closed pitch while the loosely wound sections 152 have an open pitch. In other words, the tightly wound sections 150 are formed of tightly compressed individual coils 154 of the drive cable 132 having little to no space between them, while the loosely wound sections 152 are formed by coils 154 having greater space between centers of adjacent coils 154. In some embodiments, the pitch of the coils 154 in the loosely wound sections 152 may range from 1.1938 mm (0.047 inches) to 1.3462 mm (0.053 inches). In the pictured embodiment, the loosely wound sections 152 are formed by four loosely wound turns or coils 154 of the drive cable 132. However, the loosely wound sections 152 may be formed by any number of coils 154.

In one embodiment, the drive cable 132 is manufactured by stretching a tightly compressed coil at constant intervals past the recovery point of the coil material, thereby creating alternating areas of tightly wound coil and loosely wound coil. Stretching the coil past its recovery point "sets" the intervals between the individual coils (e.g., coils 154) and creates constant intervals between the tightly wound sections 150 and the loosely wound sections 152. For example, in the pictured embodiment in FIG. 5, the tightly wound sections 150 are separated from one another by a constant interval I1, which reflects a fixed distance between adjacent tightly wound sections 150. The individual coils 154 of the loosely wound sections 152 are separated from one another by a constant interval I2, which reflects a fixed distance between adjacent loosely wound coils 154 in the loosely wound sections 152. The interval I1 may vary in different embodiments depending upon the particular application desired. For example, in various embodiments, the interval I1 may range from 0.5 cm to 5 cm. In some embodiments, the interval I1 of the drive cable 132 is 1 cm. Thus, the drive cable 132 has highly radiopaque tightly wound sections 150 alternating with less radiopaque loosely wound sections 152 at substantially constant intervals, allowing the drive cable 132 to serve as an internal marking or measuring device. In some embodiments, the drive cable 132 may be wound around a hollow and flexible tubular member to prevent unwanted kinking of the drive cable, while maintaining flexibility. In some embodiments, the hollow, flexible member may have a uniform diameter and may include a proximal portion and a distal portion with a central lumen extending therebetween.

In some embodiments, the drive cable 132 incorporating the plurality of radiopaque markers is coated with a lubricious coating 170 and/or surrounded by a polymer layer as described above in the context of FIGS. 3A, 3B, 4A, and 4B. For example, FIG. 6A illustrates a cross-sectional side view of a portion of the drive cable 132 according to an embodiment of the present disclosure where the drive cable 132 includes a plurality of radiopaque markers 140, as discussed with respect to FIGS. 4A, 4B, and 5, and is coated with a lubricious coating 170 to reduce rotational frictional forces experienced by the drive cable 132. As another example, FIG. 6B illustrates a cross-sectional side view of a portion of the drive cable 132 according to another embodiment of the present disclosure where the drive cable 132 includes a plurality of radiopaque markers 140, as discussed with respect to FIGS. 4A, 4B, and 5, and is surrounded by a polymer layer 160, which may or may not be coated with a lubricious coating 170, to reduce the rotational frictional forces experienced by the drive cable 132.

Embodiments in accordance with the present disclosure provide users with an accurate and efficient device, system, and method for evaluating, localizing, and measuring anatomical structures and/or lesions to plan an appropriate treatment course and/or evaluate a given treatment. For example, but not by way of limitation, embodiments of the present disclosure may be used to assist in evaluating an intraluminal site for implantation of a prosthesis (e.g., a drug-eluting balloon, a drug-eluting stent, a stent graft, a bioresorbable stent), PTCA balloon location, an endovascular aneurysm repair (e.g., of the abdominal or thoracic aorta), IVC filter placement (e.g., in the inferior vena cava), evaluation of tumor growth/response to treatment, and a variety of other procedures previously utilizing a separate measuring device (e.g., a ruler) for lesion measurement. In addition, embodiments of the present disclosure may be used to monitor the position and/or efficacy of already implanted devices such as, but not by way of limitation, stents, stent grafts, drug-eluting stents, drug-eluting balloons, and orthopedic implants (e.g., bone screws or hip, shoulder, or knee implants). Moreover, the present disclosure can eliminate at least one pigtail marker catheter exchange in several procedures, such as a low contrast endovascular aneurysm repair procedure, thereby accelerating the process of stent-graft length sizing assessment. Some embodiments of the present disclosure may be used in a variety of organ systems such as, but not by way of limitation, the circulatory system, the lymphatic system, the digestive system, the pulmonary system, the orthopedic system, and the neurological system.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A rotational IVUS device, comprising:
   a drive cable configured to rotate about an axis of rotation associated with the IVUS device, the drive cable comprising a proximal end, a distal end, a length from the proximal end to the distal end, and a flexible coil extending from the proximal end to the distal end, the flexible coil configured to transfer a rotational force along the length of the drive cable; and a transducer coupled to the distal end of the flexible coil such that the transducer rotates with the drive cable, wherein the flexible coil of the drive cable includes a single length of material formed into an alternating series of tightly wound sections and loosely wound sections such that the tightly wound sections are a plurality of radiopaque markers spaced from one another along the length of the drive cable.

2. The rotational IVUS device of claim 1, wherein the plurality of radiopaque markers extend along the drive cable from adjacent to the distal end to adjacent to a proximal end.

3. The rotational IVUS device of claim 1, wherein the plurality of radiopaque markers are of equal size.

4. The rotational IVUS device of claim 1, wherein the plurality of radiopaque markers are of variable size.

5. The rotational IVUS device of claim 1, wherein the plurality of radiopaque markers are spaced equidistantly along the drive cable.

6. The rotational IVUS device of claim 1, wherein the plurality of radiopaque markers are variably spaced along the drive cable.

7. The rotational IVUS device of claim 1, wherein a width of a radiopaque marker, from among the plurality of radiopaque markers, is proportional to a distance between two adjacent radiopaque markers from among the plurality of radiopaque markers.

8. The rotational IVUS device of claim 1, wherein the tightly wound sections comprise areas of a closed pitch and the loosely wound sections comprise areas of an open pitch.

9. The rotational IVUS device of claim 1, wherein the flexible coil is hollow.

10. The rotational IVUS device of claim 9, wherein the drive cable is coated with a lubricious coating configured to enable uniform rotation of the drive cable and the transducer by reducing frictional forces experienced by the drive cable.

11. The rotational IVUS device of claim 9, further comprising a polymer layer fixedly secured to and surrounding the drive cable without enclosing the transducer, wherein the polymer layer is configured to enable uniform rotation of the transducer by reducing frictional forces experienced by the drive cable.

12. The rotational IVUS device of claim 1, wherein the tightly wound sections comprise a first pitch along a lengthwise direction of the drive cable and the loosely wound sections comprise a second pitch along the lengthwise direction, the first pitch being smaller than the second pitch.

13. The rotational IVUS device of claim 12, wherein the first pitch is a closed pitch and the second pitch is an open pitch.

* * * * *